(12) United States Patent
Demirci et al.

(10) Patent No.: US 11,709,122 B2
(45) Date of Patent: Jul. 25, 2023

(54) SYSTEM AND METHOD FOR SPERM SORTING

(71) Applicant: THE BRIGHAM AND WOMEN'S HOSPITAL, INC., Boston, MA (US)

(72) Inventors: Utkan Demirci, Cambridge, MA (US); Waseem Asghar, Boston, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 0 days.

(21) Appl. No.: 17/322,464

(22) Filed: May 17, 2021

(65) Prior Publication Data
US 2021/0270715 A1 Sep. 2, 2021

Related U.S. Application Data

(63) Continuation of application No. 16/544,762, filed on Aug. 19, 2019, now Pat. No. 11,009,444, which is a
(Continued)

(51) Int. Cl.
*C12N 5/071* (2010.01)
*G01N 15/10* (2006.01)
(Continued)

(52) U.S. Cl.
CPC ........ *G01N 15/10* (2013.01); *B01L 3/502753* (2013.01); *C12N 5/061* (2013.01);
(Continued)

(58) Field of Classification Search
CPC ................. C12M 21/06; C12N 5/0612; G01N 2800/367
See application file for complete search history.

(56) References Cited

U.S. PATENT DOCUMENTS

| 5,028,526 A | 7/1991 | Deutsch |
| 5,296,375 A | 3/1994 | Kricka |

(Continued)

FOREIGN PATENT DOCUMENTS

| CN | 103937658 A | 7/2014 |
| CN | 104099293 A | 10/2014 |

(Continued)

OTHER PUBLICATIONS

Morbeck, Dean E., et al. "Sperm morphology: classification drift over time and clinical implications." Fertility and Sterility 96.6 (2011): 1350-1354.
(Continued)

*Primary Examiner* — Jonathan M Hurst
(74) *Attorney, Agent, or Firm* — Quarles & Brady LLP

(57) ABSTRACT

A system and method for sorting sperm is provided. The system includes a housing and a microfluidic system supported by the housing. The system also includes an inlet providing access to the microfluidic system to deliver sperm to the microfluidic system and an outlet providing access to the microfluidic system to harvest sorted sperm from the microfluidic system. The microfluidic system provides a flow path for sperm from the inlet to the outlet and includes at least one channel extending from the inlet to the outlet to allow sperm delivered to the microfluidic system through the inlet to progress along the flow path toward the outlet. The microfluidic system also includes a filter including a first plurality of micropores arranged in the flow path between the inlet and the outlet to cause sperm traveling along the flow path to move against through the filter and gravity to reach the outlet.

23 Claims, 9 Drawing Sheets

Related U.S. Application Data continuation of application No. 15/037,844, filed as application No. PCT/US2014/066405 on Nov. 19, 2014, now Pat. No. 10,422,737.

(60) Provisional application No. 61/906,740, filed on Nov. 20, 2013.

(51) Int. Cl.
| | |
|---|---|
| *G01N 15/00* | (2006.01) |
| *B01L 3/00* | (2006.01) |
| *G01N 1/40* | (2006.01) |
| *C12N 5/076* | (2010.01) |
| *C12M 3/00* | (2006.01) |

(52) U.S. Cl.
CPC ......... *C12N 5/0612* (2013.01); *G01N 1/4005* (2013.01); *G01N 15/00* (2013.01); *C12M 21/06* (2013.01); *G01N 2001/4088* (2013.01); *G01N 2015/0003* (2013.01); *G01N 2015/0065* (2013.01); *G01N 2015/1006* (2013.01); *G01N 2015/1081* (2013.01); *G01N 2800/367* (2013.01)

(56) References Cited

U.S. PATENT DOCUMENTS

| | | | |
|---|---|---|---|
| 5,744,366 | A | 4/1998 | Kricka |
| 6,129,214 | A | 10/2000 | Bar-Ami |
| 6,391,654 | B1 | 5/2002 | Bateman |
| 6,929,945 | B2 | 8/2005 | Aravanis |
| 2004/0059186 | A1 | 3/2004 | Weichselbaum |
| 2005/0158700 | A1* | 7/2005 | Brickwood ............ C12N 5/061 435/287.1 |
| 2005/0165270 | A1 | 7/2005 | Weichselbaum |
| 2006/0270021 | A1* | 11/2006 | Takayama ........... B01L 3/50273 435/283.1 |
| 2010/0291535 | A1 | 11/2010 | Yao |
| 2012/0118740 | A1 | 5/2012 | Garcia |
| 2012/0122084 | A1 | 5/2012 | Wagner |
| 2014/0315281 | A1 | 10/2014 | Pan |
| 2015/0132755 | A1* | 5/2015 | Kirschhoffer ....... B01L 3/50255 435/7.1 |

FOREIGN PATENT DOCUMENTS

| | | | |
|---|---|---|---|
| EP | 0639223 | | 2/1995 |
| WO | 1993022421 | | 11/1993 |
| WO | 2001060968 | | 8/2001 |
| WO | 0220713 | A1 | 3/2002 |
| WO | 2005027634 | A1 | 3/2005 |
| WO | 2007129292 | A1 | 11/2007 |
| WO | 2008121437 | A2 | 10/2008 |
| WO | WO-2012126478 | A1 * | 9/2012 ........ B01L 3/502761 |
| WO | 2012162181 | A2 | 11/2012 |
| WO | 2013040428 | A1 | 3/2013 |
| WO | 2013129947 | A1 | 9/2013 |
| WO | 2014177157 | A1 | 11/2014 |

OTHER PUBLICATIONS

Muratori, Monica, et al. "Spontaneous DNA fragmentation in swim-up selected human spermatozoa during long term incubation." Journal of Andrology 24.2 (2003): 253-262.

Noguchi, Hiroshi, et al. "Fluid vesicles with viscous membranes in shear flow." Physical Review letters 93.25 (2004): 258102.

Noguchi, Hiroshi. "Dynamic modes of microcapsules in steady shear flow: effects of bending and shear elasticities." Physical Review E 81.5 (2010): 056319.

Noguchi, Hiroshi. "Dynamic modes of red blood cells in oscillatory shear flow." Physical Review E 81.6 (2010): 061920.

O'Connell, M., et al. "The effects of cryopreservation on sperm morphology, motility and mitochondrial function." Human Reproduction 17.3 (2002): 704-709.

Ombelet, Willem, et al. "Infertility and the provision of infertility medical services in developing countries." Human Reproduction Update 14.6 (2008): 605-621.

Palermo, Gianpiero, et al. "Pregnancies after intracytoplasmic injection of single spermatozoon into an oocyte." The Lancet 340.8810 (1992): 17-18.

PCT International Search Report and Written Opinion, PCT/US2014/066405, dated Mar. 3, 2015.

Petersen, Matt K., et al. "Mesoscale hydrodynamics via stochastic rotation dynamics: Comparison with Lennard-Jones fluid." The Journal of Chemical Physics 132.17 (2010): 174106.

Rajfer, Jacob. "Sperm health in the aging male." Reviews in Urology 8.2 (2006): 87.

Riedel-Kruse, Ingmar H., et al. "How molecular motors shape the flagellar beat." HFSP Journal 1.3 (2007): 192-208.

Rijsselaere, Tom, et al. "Effect of centrifugation on in vitro survival of fresh diluted canine spermatozoa." Theriogenology 57.6 (2002): 1669-1681.

Sakkas, Denny. "Novel technologies for selecting the best sperm for in vitro fertilization and intracytoplasmic sperm injection." Fertility and Sterility 99.4 (2013): 1023-1029.

Schuster, Timothy G., et al. "Isolation of motile spermatozoa from semen samples using microfluidics." Reproductive BioMedicine Online 7.1 (2003): 75-81.

Shi, Linda Z., et al. "Computer-based tracking of single sperm." Journal of Biomedical Optics 11.5 (2006): 054009.

Shittu L A. J., et al., "Pregnancy outcome following swim up preparation of both fresh and cryopreserved spermatozoa." Scientific Research and Essays 1.3 (2006): 103-107.

Shoukir, Youssef, et al. "Blastocyst development from supernumerary embryos after intracytoplasmic sperm injection: a paternal influence?." Human Reproduction (Oxford, England) 13.6 (1998): 1632-1637.

Sun, Jian-Guo, et al. "Detection of deoxyribonucleic acid fragmentation in human sperm: correlation with fertilization in vitro." Biology of Reproduction 56.3 (1997): 602-607.

Tao, Yu-Guo, et al. "Multiparticle collision dynamics modeling of viscoelastic fluids." The Journal of Chemical Physics 128.14 (2008): 144902.

Tasoglu, Savas, et al. "Exhaustion of Racing Sperm in Nature-Mimicking Microfluidic Channels During Sorting." Small 9.20 (2013): 3374-3384.

Tasoglu, Savas, et al. "Manipulating biological agents and cells in micro-scale volumes for applications in medicine." Chemical Society Reviews 42.13 (2013): 5788-5808.

Tucci, Kay, et al. "Mesoscopic model for diffusion-influenced reaction dynamics." The Journal of Chemical Physics 120.17 (2004): 8262-8270.

Tüzel, E., et al. "Mesoscopic model for the fluctuating hydrodynamics of binary and ternary mixtures." EPL (Europhysics Letters) 80.4 (2007): 40010.

Tüzel, E., et al. "Transport coefficients for stochastic rotation dynamics in three dimensions." Physical Review E 68.3 (2003): 036701.

Tüzel, Erkan, et al. "Constructing thermodynamically consistent models with a non-ideal equation of state." Mathematics and Computers in Simulation 72.2-6 (2006): 232-236.

Tüzel, Erkan, et al. "Dynamics of thermally driven capillary waves for two-dimensional droplets." The Journal of Chemical Physics 132.17 (2010): 174701.

Tuzel, Erkan. Particle-based mesoscale modeling of flow and* transport in complex fluids, Ph.D. Thesis, University of Minnesota, 2006, 24 pages.

Van Den Bergh, Marc, et al. "A first prospective study of the individual straight line velocity of the spermatozoon and its influences on the fertilization rate after intracytoplasmic sperm injection." Human Reproduction (Oxford, England) 13.11 (1998): 3103-3107.

(56) References Cited

OTHER PUBLICATIONS

Wikland, M., et al. "A self-migration method for preparation of sperm for in-vitro fertilization." Human Reproduction 2.3 (1987): 191-195.
World Health Organization, Department of Reproductive Health and Research. "WHO laboratory manual for the Examination and processing of human sperm." World Health Organiz, (2010).
Xie, Lan, et al. "Integration of sperm motility and chemotaxis screening with a microchannel-based device." Clinical Chemistry 56.8 (2010): 1270-1278.
Xu, De-Xiang, et al. "The associations among semen quality, oxidative DNA damage in human spermatozoa and concentrations of cadmium, lead and selenium in seminal plasma." Mutation Research/Genetic Toxicology and Environmental Mutagenesis 534.1 (2003): 155-163.
Yang, Yingzi, et al. "Cooperation of sperm in two dimensions: synchronization, attraction, and aggregation through hydrodynamic interactions." Physical Review E 78.6 (2008): 061903.
Zare, Richard N., et al. "Microfluidic platforms for single-cell analysis." Annual Review of Biomedical Engineering 12 (2010): 187-201.
Zhang, Xiaohui, et al. "Lensless imaging for simultaneous microfluidic sperm monitoring and sorting." Lab on a Chip 11.15 (2011): 2535-2540.
Zini, Armand, et al. "Influence of semen processing technique on human sperm DNA integrity." Urology 56.6 (2000): 1081-1084.
Abbey, A. et al. "Gender's role in responses to infertility." Psychology of Women Quarterly 15.2 (1991): 295-316.
Ainsworth, C. et al. "Development of a novel electrophoretic system for the isolation of human spermatozoa." Human Reproduction 20.8 (2005): 2261-2270.
Aitken, R. J., et al. "On methods for the detection of reactive oxygen species generation by human spermatozoa: analysis of the cellular responses to catechol oestrogen, lipid aldehyde, menadione and arachidonic acid." Andrology 1.2 (2013): 192-205.
Aitken, R. J., et al. "The source and significance of DNA damage in human spermatozoa; a commentary on diagnostic strategies and straw man fallacies." MHR: Basic Science of Reproductive Medicine 19.8 (2013): 475-485.
Aitken, R., et al. "Significance of reactive oxygen species and antioxidants in defining the efficacy of sperm preparation techniques." Journal of Andrology 9.6 (1988): 367-376.
Akl, Livia D., et al. "Efficacy of the motile sperm organelle morphology examination (MSOME) in predicting pregnancy after intrauterine insemination." Reproductive Biology and Endocrinology 9.1 (2011): 120.
Asghar W et al., "Selection of functional human sperm with higher DNA integrity and fewer reactive oxygen species", NIH Author Manuscript PMC4194169 URL: https://www.ncbi.nlm.nih.gov/pmc/articles/PMC4194169/ Published in final form in Advanced Healthcare Material, 2014, 3(10):1671-1679.
Auger, J., et al. "Sperm morphological defects related to environment, lifestyle and medical history of 1001 male partners of pregnant women from four European cities." Human Reproduction 16.12 (2001): 2710-2717.
Australian Government IP Australia Examination Report No. 1 for application 2014353050, dated Dec. 11, 2018.
Australian Government IP Australia Examination Report No. 2 for application 2014353050, dated Mar. 21, 2019.
Bartoov, Benjamin, et al. "Real-Time Fine Morphology of Motile Human Sperm Cells is Associated With IVF-ICSI Outcome." Journal of Andrology 23.1 (2002): 1-8.
Berkovitz, A., et al. "Howto improve IVF-ICSI outcome by sperm selection." Reproductive BioMedicine Online 12.5 (2006): 634-638.
Bland, J. M. et al. "Statistical methods for assessing agreement between two methods of clinical measurement." The Lancet 327. 8476 (1986): 307-310.

Boivin, Jacky, et al. "International estimates of infertility prevalence and treatment-seeking: potential need and demand for infertility medical care." Human Reproduction 22.6 (2007): 1506-1512.
Brown, David B., et al. "Evaluating a novel panel of sperm function tests for utility in predicting intracytoplasmic sperm injection (ICSI) outcome." Journal of Assisted Reproduction and Genetics 30.4 (2013): 461-477.
Brugh III, Victor M., et al. "Male factor infertility: evaluation and management." Medical Clinics of North America 88.2 (2004): 367-385.
Burnett La et al, "Two types of assays for detecting frog sperm chemoattraction", Journal of Visualized Experiments, 2011, (58):e3407. doi: 10.3791/3407.
Canadian Intellectual Property Office, Office Action for application 2,931,201, dated Sep. 16, 2019.
Carlsen, Elisabeth, et al. "Evidence for decreasing quality of semen during past 50 years." BMJ 305.6854 (1992): 609-613.
Chan, Philip J., et al. "A simple zeta method for sperm selection based on membrane charge." Fertility and Sterility 85.2 (2006): 481-486.
China National Intellectual Property Office, First Office Action for application 201480073593, dated Mar. 26, 2019, with translation.
Cho, Brenda S., et al. "Passively driven integrated microfluidic system for separation of motile sperm." Analytical Chemistry 75.7 (2003): 1671-1675.
Cooper, Trevor G., et al. "World Health Organization reference values for human semen characteristics." Human Reproduction Update 16.3 (2010): 231-245.
Corkidi, G., et al. "Tracking sperm in three-dimensions." Biochemical and Biophysical Research Communications 373.1 (2008): 125-129.
De Iuliis, Geoffry N., et al. "DNA damage in human spermatozoa is highly correlated with the efficiency of chromatin remodeling and the formation of 8-hydroxy-2'-deoxyguanosine, a marker of oxidative stress." Biology of Reproduction 81.3 (2009): 517-524.
De Iuliis, Geoffry N., et al. "Mobile phone radiation induces reactive oxygen species production and DNA damage in human spermatozoa in vitro." PloS one 4.7 (2009): e6446.
De Vos, Anick, et al. "Influence of individual sperm morphology on fertilization, embryo morphology, and pregnancy outcome of intracytoplasmic sperm injection." Fertility and Sterility 79.1 (2003): 42-48.
Elgeti, Jens, et al. "Hydrodynamics of sperm cells near surfaces." Biophysical Journal 99.4 (2010): 1018-1026.
European Patent Office, Extended European Search Report, Application No. 14864395.0, dated Sep. 4, 2017.
Fisher, H. S., et al. "Competition drives cooperation among closely related sperm of deer mice." Nature 463.7282 (2010): 801.
Foresta, C., et al. "Sperm nuclear instability and staining with aniline blue: abnormal persistance of histones in spermatozoa in infertile men." International Journal of Andrology 15.4 (1992): 330-337.
Frey, Keith A. "Male reproductive health and infertility." Primary Care: Clinics in Office Practice 37.3 (2010): 643-652.
Gompper, G., et al. "Multi-particle collision dynamics: a particle-based mesoscale simulation approach to the hydrodynamics of complex fluids." Advanced computer simulation approaches for soft matter sciences III. Springer, Berlin, Heidelberg, 2009. 1-87.
Götze, Ingo O., et al. "Mesoscale simulations of hydrodynamic squirmer interactions." Physical Review E 82.4 (2010): 041921.
Grassia, P. S., et al. "Computer simulations of Brownian motion of complex systems." Journal of Fluid Mechanics 282 (1995): 373-103.
Grunewald, Sonja, et al. "Sperm Processing and Selection." Male Infertility. Springer, New York, NY, 2012. 423-430.
Hammadeh, M. E., et al. "Association between sperm cell chromatin condensation, morphology based on strict criteria, and fertilization, cleavage and pregnancy rates in an IVF program." Andrologia 30.1 (1998): 29-35.

(56) References Cited

OTHER PUBLICATIONS

Hammadeh, M. E., et al. "Predictive value of sperm chromatin condensation (aniline blue staining) in the assessment of male fertility." Archives of Andrology 46.2 (2001): 99-104.

Henkel, Ralf R., et al. "Sperm preparation for ART." Reproductive Biology and Endocrinology 1.1 (2003): 108.

Henkel, Ralf. "Sperm preparation: state-of-the-art—physiological aspects and application of advanced sperm preparation methods." Asian Journal of Andrology 14.2 (2012): 260-269.

Ihle, T., and D. M. Kroll. "Stochastic rotation dynamics: a Galilean-invariant mesoscopic model for fluid flow." Physical Review E 63.2 (2001): 020201.

Ihle, Thomas, et al. "Resummed Green-Kubo relations for a fluctuating fluid-particle model." Physical Review E 70.3 (2004): 035701.

Japanese Patent Office, Office Action for application 2016-533083, dated Oct. 2, 2018, with translation.

Kapral, Raymond. "Multiparticle collision dynamics: simulation of complex systems on mesoscales." Advances in Chemical Physics 140 (2008): 89-146.

Kricka, L. J., et al. "Applications of a microfabricated device for evaluating sperm function." Clinical Chemistry 39.9 (1993): 1944-1947.

Lauga, Eric, et al. "The hydrodynamics of swimming microorganisms." Reports on Progress in Physics 72.9 (2009): 096601.

Malevanets, Anatoly, et al. "Mesoscopic model for solvent dynamics." The Journal of Chemical Physics 110.17 (1999): 8605-8613.

Messlinger, Sebastian, et al. "Dynamical regimes and hydrodynamic lift of viscous vesicles under shear." Physical Review E 80.1 (2009): 011901.

Miller, Jane E., et al. "The effect of intracytoplasmic sperm injection and semen parameters on blastocyst development in vitro." Human Reproduction 16.5 (2001): 918-924.

Monqaut, Ana Laura, et al. "Use of high-magnification microscopy for the assessment of sperm recovered after two different sperm processing methods." Fertility and Sterility 95.1 (2011): 277-280.

Bahat et al., "Thermotaxis of Human Sperm Cells in Extraordinarily Shallow Temperature Gradients Over a Wide Range", PLos ONE, Jul. 2012, vol. 7, Issue 7, e41915, 9 pages.

Wei, H. et al. "Particle sorting using a porous membrane in a microfluidic device." Lab on a Chip 11 (2011): 238-245.

\* cited by examiner

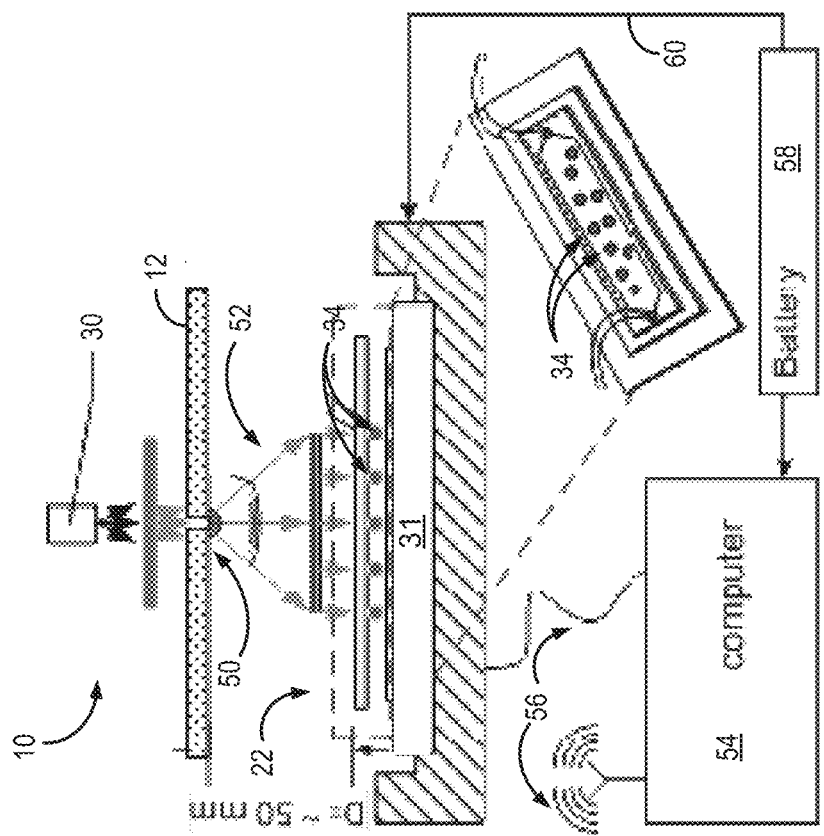
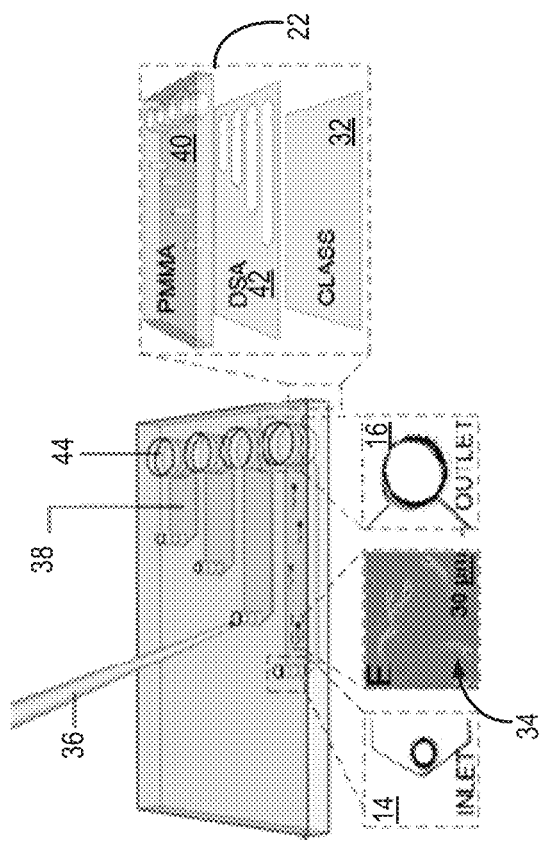
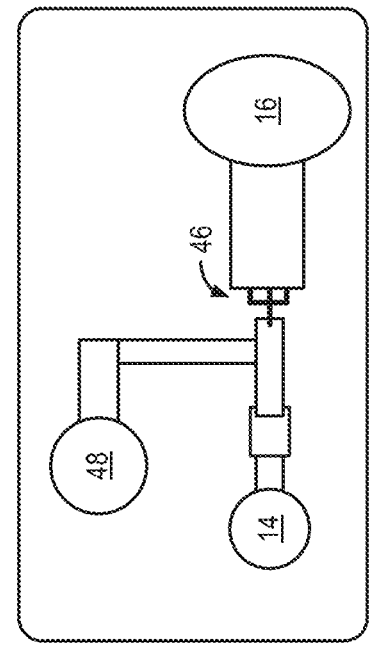
FIG. 2B
FIG. 2C
FIG. 2D

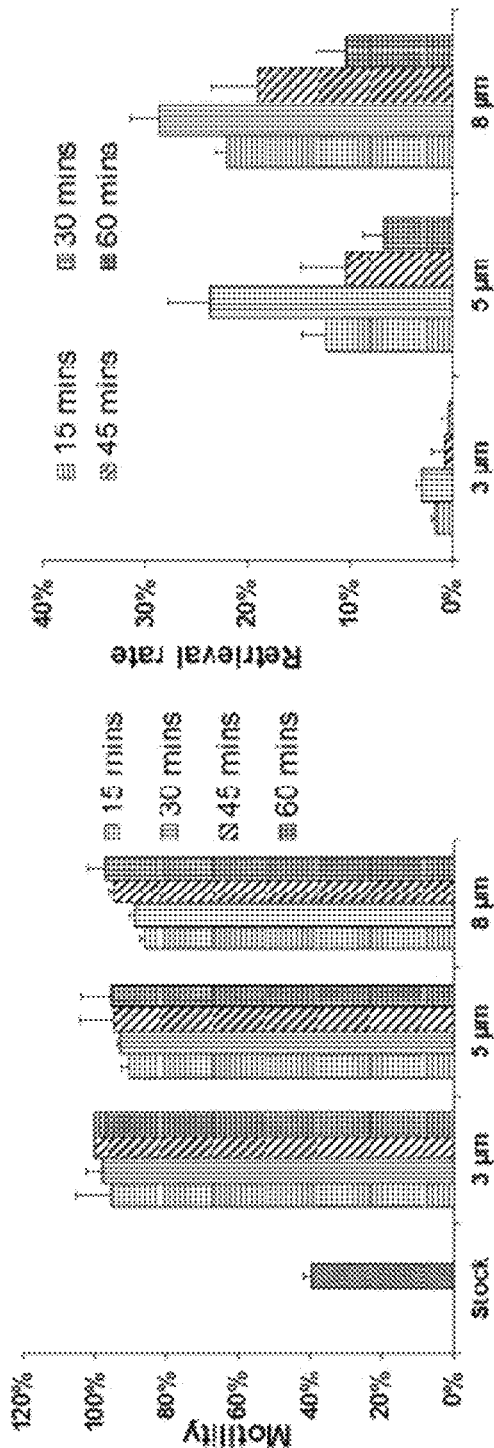
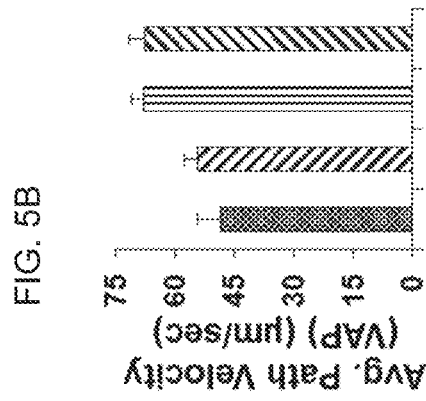
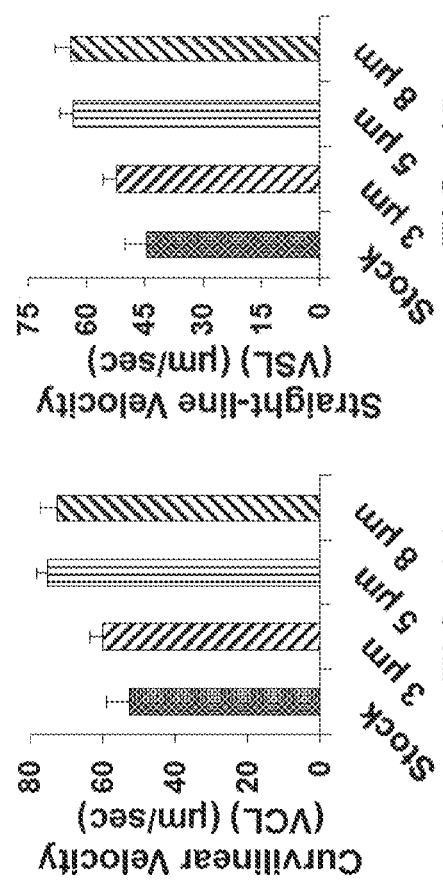

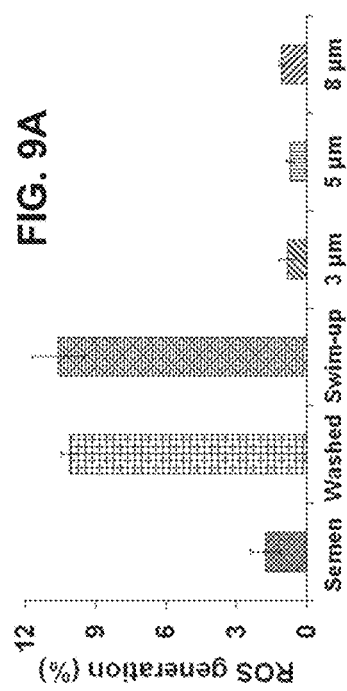
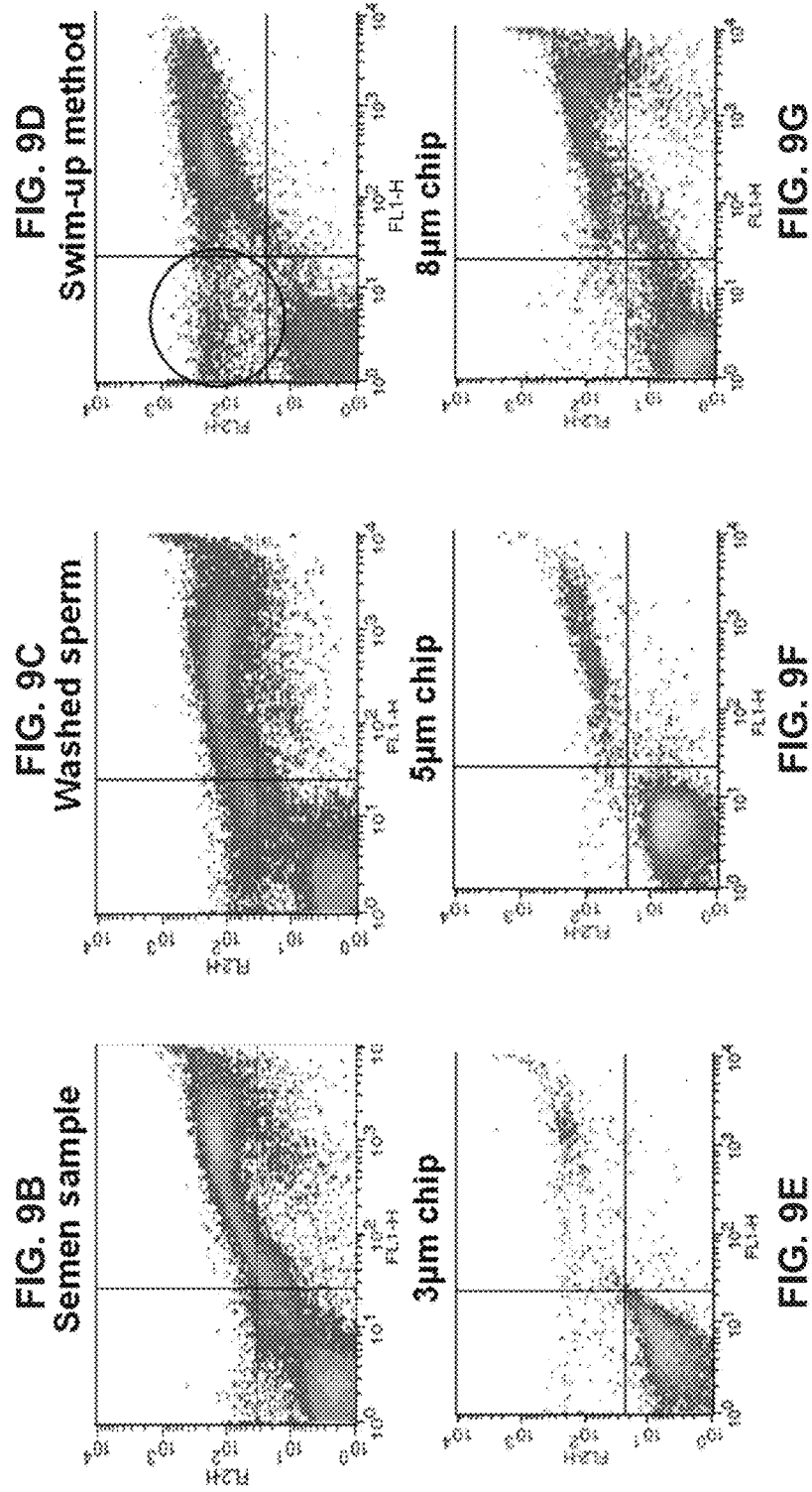

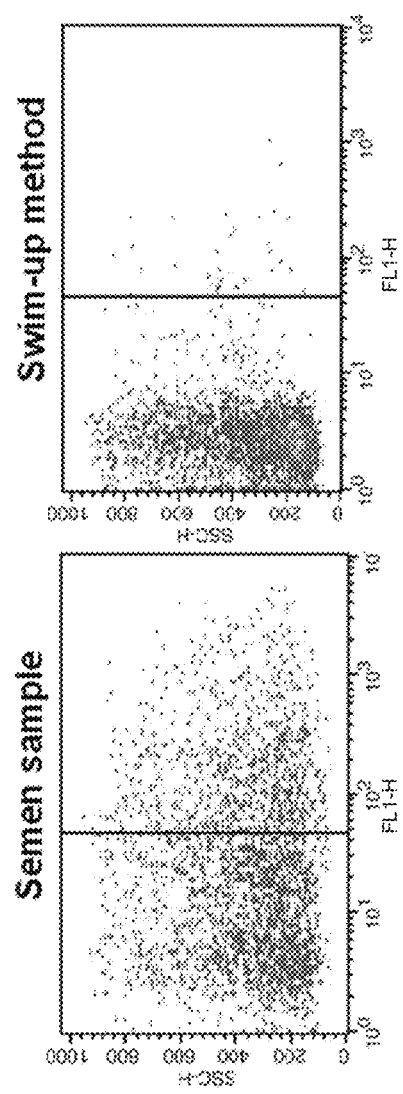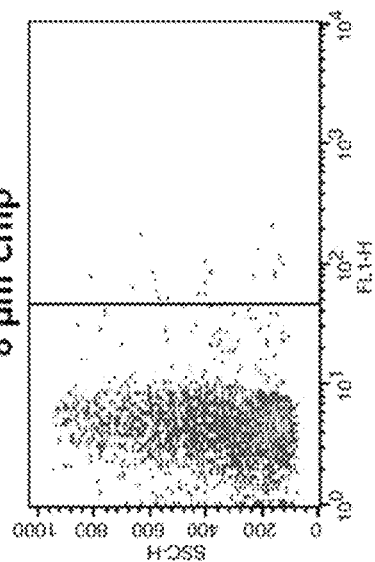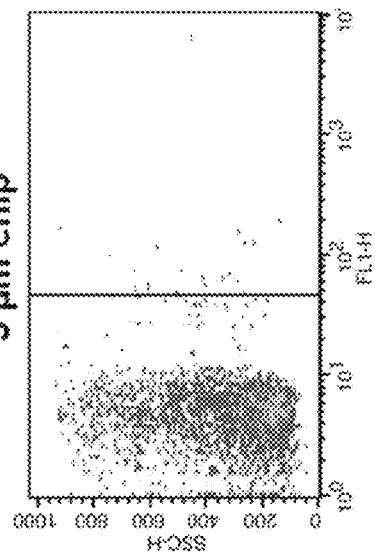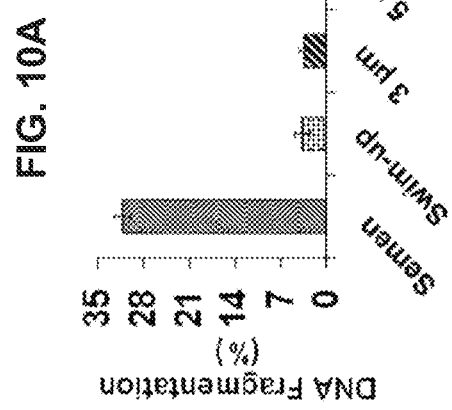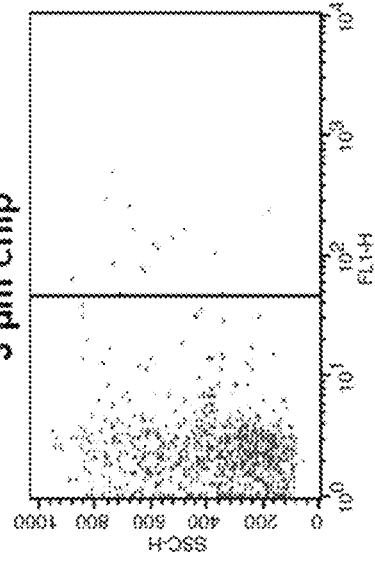

SYSTEM AND METHOD FOR SPERM SORTING

CROSS-REFERENCE TO RELATED APPLICATIONS

This application is a continuation of U.S. patent application Ser. No. 16/544,762, filed Aug. 19, 2019, which is a continuation of U.S. patent application Ser. No. 15/037,844, filed May 19, 2016 and issued as U.S. Pat. No. 10,422,737 on Sep. 24, 2019, which represents the U.S. National Stage of International Application PCT/US2014/066405, filed Nov. 19, 2014, which claims priority to U.S. Provisional Application 61/906,740, filed Nov. 20, 2013, all of which are incorporated herein by reference for all purposes."

STATEMENT REGARDING FEDERALLY SPONSORED RESEARCH

This invention was made with government support under grant number EB015776 awarded by the National Institutes of Health. The government has certain rights in the invention.

STATEMENT REGARDING FEDERALLY SPONSORED RESEARCH

N/A

BACKGROUND OF THE INVENTION

The present invention relates generally to systems and methods for sperm sorting.

According to estimates, there are more than 70 million infertile couples worldwide. Approximately 1 in every 4 infertile couples seek clinical treatment, where, according to sources, male factor may account for about 50 percent of the infertility cases. Assisted reproductive technology (ARTs), such as in vitro fertilization (IVF), intracytoplasmic sperm injection (ICSI), and intrauterine insemination (IUI), are generally utilized in reproductive clinics to treat infertile couples. With an increasing rate of male infertility due to environmental and physiological conditions, there is an ever growing need for the use of ARTs in reproductive clinics. Isolation of the most motile and morphologically normal sperm is an integral process to commonly used IVF/ICSI procedures. Selection of healthy sperm from unprocessed semen (stock sperm) is crucial as it requires selecting sperm that is not only highly motile, but also has a normal morphology, mature nuclei, and lesser reactive oxygen species (ROS) production. Although current IVF/ICSI procedures results in successful pregnancy approximately 50 percent of the time, the output can be greatly compromised if the sperm being selected are abnormal.

Currently, the more commonly-known ART techniques use centrifugation based sperm swim-up, density gradient separation methods, and microfluidic based methods with/without the use of chemotaxis to sort sperm. These techniques have potential drawbacks and limitations in their use for procedures as delicate as IVF/ICSI. It is worth noting that the centrifugation based sperm sorting techniques, such as swim-up, compromise on sperm quality during the repetitive centrifugation steps. Quality of a sperm sample is degraded during swim-up technique due to ROS generation. ROS exposure can greatly harm the DNA of seemingly motile and healthy sperm. Furthermore, the centrifugation-based sperm sorting techniques are labor intensive, and outcome can vary from technician to technician.

Sperm sorting technologies based on microfluidics have an advantage because they can precisely handle small volume of sperm samples. On the other hand, microfluidic-based sperm sorting devices have very low throughput and can only process small semen volumes, such as 2 μl-50 μl, which limits their application to reproductive clinics, where normal sperm sample can have volume of ≥1.5 ml.

In a clinical ICSI procedure, an embryologist will have on average 20 oocytes that can be handled in four petri dishes, and will need 20 sperm. The embryologist would like to choose these 20 sperm in an oligospermic sample among a few hundred sperm. Such scenario would require real-time monitoring of individual sperm and collection from outlet when 20 sperm reach the outlet, which is not attainable using current clinical or microfluidic technologies. In a second procedure, where an embryologist is handling healthy samples, in vitro fertilization is performed using 0.5 million healthy sperm suspended in a 5-20 μl suspension to be introduced to an oocyte. However, current sorting systems, such as described above, do not provide the throughput needed to meet these criteria.

Traditionally, optical microscopes have been used to image sperm for computer assisted sperm analysis (CASA) and manual identification of sperm motility for ARTs. This classical approach has limitations in tracking a large number of sperm simultaneously due to its small field of view (FOV). In addition, sperm tracking and motility analyses are performed after sorting. Currently no system exists that can sort and analyze sperm simultaneously.

It would therefore be desirable to provide a system and method for processing, including as sorting, sperm without damaging the sperm or subjecting the sperm to potentially-damaging conditions. Furthermore, it would be desirable to provide a system and method that can analyze sperm, but is efficient and able to scale.

SUMMARY OF THE INVENTION

The present invention overcomes the aforementioned drawbacks by providing a system and method that integrates micro- and macro-fluidics to sort sperm in a manner that allows efficient selection of sperm that are favorably suited to fertilization. In particular, the present invention recognizes that sperm suited to fertilization is most desirable and can be selected or sorted using a system presents and environment that is akin to that presented in the fertilization process. In this regard, a system is provided where macro reservoirs are connected by micropores to approximate the female genital track. A system and method is provide whereby the most motile, morphologically normal, mature, and functional sperm pass selectively through the micropores against gravity leaving behind dead or less functional sperm. The present invention is a chemical-free, centrifugation-free, and flow-free technology, where functional sperm are isolated from unprocessed semen sample with high retrieval rate.

In accordance with one aspect of the invention, a system for sorting sperm is provided that includes a housing and a microfluidic system supported by the housing. The system also includes an inlet providing access to the microfluidic system to deliver sperm to the microfluidic system and an outlet providing access to the microfluidic system to harvest sorted sperm from the microfluidic system. The microfluidic system provides a flow path for sperm from the inlet to the outlet and includes at least one channel extending from the inlet to the outlet to allow sperm delivered to the microfluidic system through the inlet to progress along the flow path toward the outlet. The microfluidic system also includes a filter including a plurality of micropores and arranged in the flow path between the inlet and the outlet to cause sperm traveling along the flow path to move against the filter and gravity to reach the outlet.

In accordance with another aspect of the invention, a method for sorting sperm is disclosed that includes delivering a sample of sperm to an inlet connected to a microfluidic system and allowing sperm in the sample of sperm to traverse a flow path through the microfluidic system toward an outlet providing access to the microfluidic system to harvest sorted sperm from the microfluidic system. The method also includes filtering the sperm prior to reaching the outlet using a filter having a plurality of micropores and gravity to restrict movement of the sperm through the filter. The method further includes harvesting sperm passing to the outlet after passing through the filter and overcoming gravity.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 2B is a detailed, perspective view of a microfluidic system of FIG. 1A or 2A.

FIG. 2C is a schematic view of a multi-channel microfluidic system in accordance with the present invention.

FIG. 2D is a cross-sectional view of overall system for sperm sorting and imaging system in accordance with the present invention.

FIG. 5A is graph illustrating motility of human sperm isolated using different pore diameter filters and retrieved at different time points FIG. 5B is a graph illustrating retrieval rate of sorted sperm using different chips.

FIGS. 6A, 6B, and 6C are graphs illustrating curvilinear velocity (VCL), straight line velocity (VSL), and average path velocity (VAP) of stock and sorted sperm using 3, 5, and 8 μm MMSS chips, respectively.

FIG. 9A is a graph showing sperm sorted using 3, 5, and 8 μm filter devices showed significantly lesser ROS generation compared to swim-up and washing methods.

FIGS. 9B through 9G are reactive oxygen species (ROS) generation graphs for (B) Semen sample, (C) Washed sperm, (D) Sperm sorted using swim-up method (ROS region is highlighted by circle), (E) Sperm sorted using 3 μm MMSS chip, (F) Sperm sorted using 5 μm MMSS chip, and (G) Sperm sorted using 8 μm MMSS chip.

FIG. 10A is a graph showing sperm sorted using 5 and 8 μm MMSS chips showed significantly lesser DNA fragmentation compared to swim-up and unsorted semen sample.

FIGS. 10B through 10F are DNA fragmentation scatter plots for (B) Semen sample, (C) Sperm sorted using swim-up method, (D) Sperm sorted using 3 μm MMSS chip, (E) Sperm sorted using 5 μm MMSS chip, and (F) Sperm sorted using 8 μm MMSS chip.

DETAILED DESCRIPTION OF THE INVENTION

The present invention recognizes that the vaginal mucus becomes watery and forms tiny microchannels that help guide sperm through to the egg. The present invention recognizes exhaustion as a mechanism for sorting sperm and has been experimentally and theoretically demonstrated to leverage exhaustion to sort healthy sperm using coarse-grained multi-scale simulation. Specifically, the present invention provides a macro-micro fluidic sperm sorting (MMSS) system to efficiently, reliably, and successfully sort sperm. As will be described, healthy motile sperm is fully collected at the outlets post-sorting. This system improves the efficiency of sperm selection process with minimal perturbation, thereby controlling against DNA fragmentation, accumulation of debris, and generation of ROS.

In addition, the present invention can simultaneously sort, monitor, and evaluate sperm. Specifically, the present system enables evaluation of each sperm individually, for example, based on velocity response, using a wide field-of-view (FOV) lensless imaging technology. The system provides a microchip-based, wide-FOV, lensless technology utilizing shadow imaging. Additionally, the present invention can be used to harvest morphometrical information, which is a reliable indicator of male fertility.

Figure 1A:
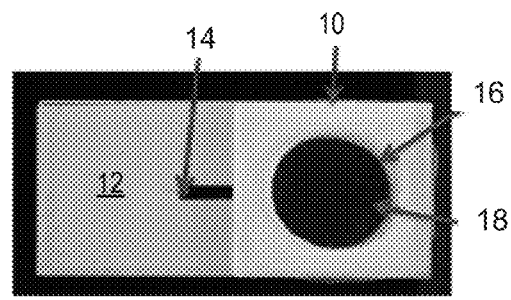
FIG. 1A is a plan view of a sperm sorting system in accordance with the present invention.
Figure 1B:
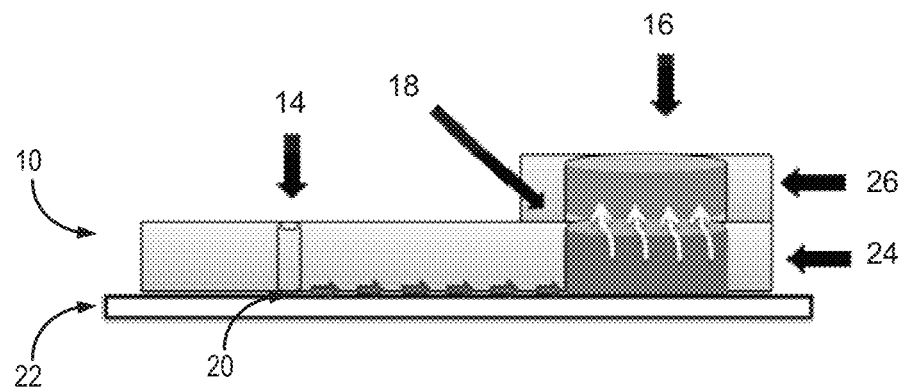
FIG. 1B is a cross-sectional view of the system of FIG. 1A.

Referring to FIG. 1A, a sperm sorting system 10 is illustrated. The system 10 may be a polydimethylsiloxane—(PDMS) based, polymethylmethacrylate—(PMMA) based, or other microfluidic system. The system 10 includes a housing 12 having an inlet 14 and a collection chamber 16 having a filter 18 arranged therein. The filter 18 may be a polycarbonate filter or other filter having suitable materials properties, such as pore or passage size, as will be described. Referring to FIG. 1B, the inlet 14 and collection chamber 16 are connected through a passage or flow path 20 extending along a microfluidic chip 22. As will be described, the microfluidic chip 22 may include a microchip that may be disposable and that handles unprocessed semen samples (either fresh or frozen, processed or raw), for example of 10 μl-3 ml, and sorts sperm rapidly, such as in less than 30 minutes, without the need for complex instrumentation or trained operators.

The flow path 20 extends from the inlet 14 to the collection chamber 16. At the collection chamber 16 a first or bottom chamber 24 is located proximate to the microfluidic chip 22 and a second or top chamber 26 is located distally with respect to the microfluidic chip 22, above the first or bottom chamber 24. As will be described, the first chamber 24 is designed to collect the semen of a sample, whether fresh or frozen, processed or raw, presented to the inlet 14 and the second chamber 26 is designed to filter the motile sperms.

Figure 1C:
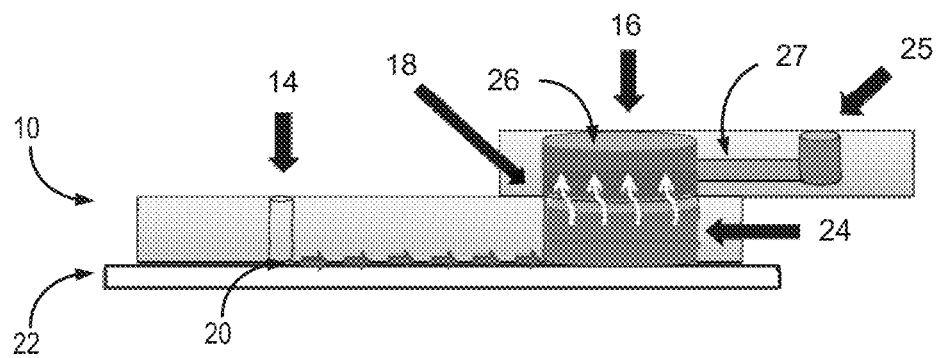
FIG. 1C is a schematic view of multichannel system with a collection chamber to concentrate the sorted sperm.

Referring to FIG. 1C, the system described above with respect to FIG. 1B may be modified to include an additional collection or "concentration" chamber 25 that is connected to the top chamber by a fluid connection 27. That is, in this regard, the sperm may be concentrated in the collection chamber 25 to facilitate easier harvesting.

Figure 1D:
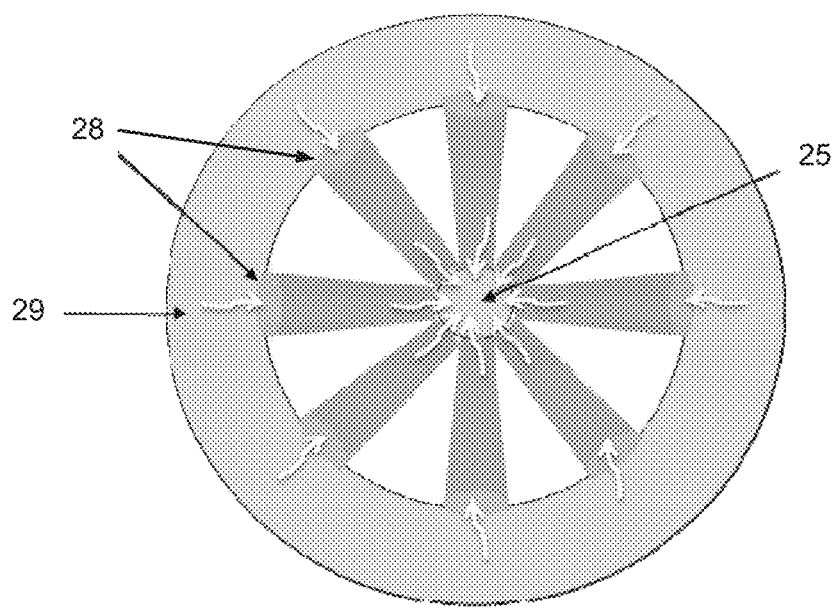
FIG. 1D is a schematic view of multi-well system with multiple channels connecting the inlet and collection or concentration chamber chamber.

In another configuration, as illustrated in FIG. 1D, the collection chamber 25 may be connected through a plurality of channels 28 each having an inlet 29 opposite the concentration chamber 25. In this regard, sperm from multiple flow paths 20 of FIG. 1C or from multiple collection chambers 16 may be delivered to a common concentration chamber 25. Such variations on the above-described design can be used to facilitate the use of multiple filters and multiple channels to handle even larger volumes or for higher throughput applications.

Figure 2A:
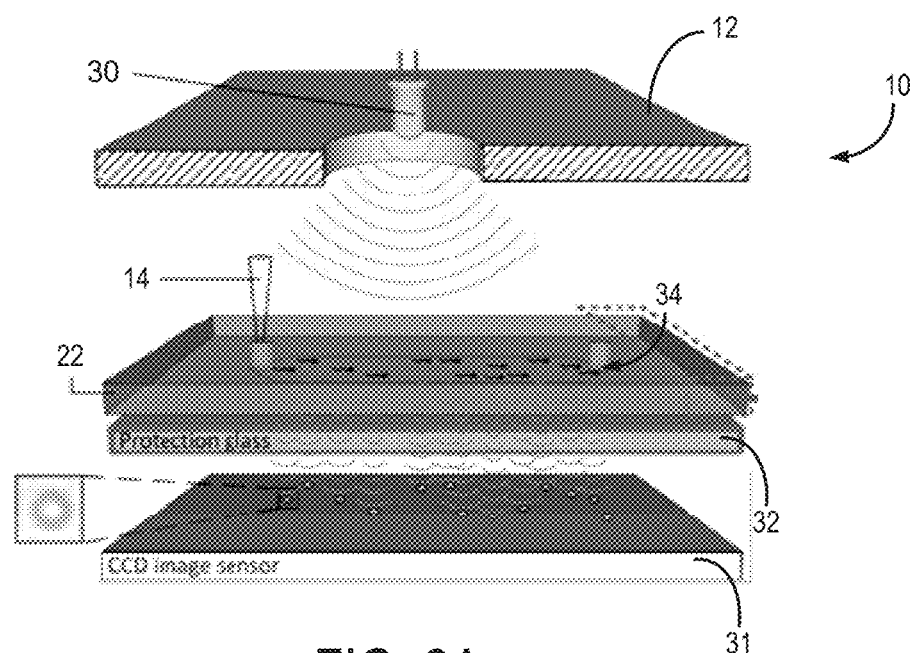
FIG. 2A is an exploded, cross-sectional view of a sperm sorting and imaging system in accordance with the present invention.

Referring to FIG. 2A, an exploded view of one optional configuration of the system 10 that includes an integrated imaging system is illustrated. The imaging system may form a lensless, wide-FOV imaging platform. In this view, components of the integrated imaging system, such as a light 30, an imaging sensor 31, and a glass protection layer 32 combined with the above-described system 10. In function, the light 30 illuminates sperm 34 introduced to the microfluidic chip 22 through the inlet 14. The illuminated sperm 34 can be imaged by the imaging sensor 31, which may be a charge-coupled device (CCD), complementary metal-oxide-semiconductor (CMOS), or other imaging device. More, specifically, referring to FIG. 2B, in function, sperm and semen 34 may be introduced into the outlet 14 using, for example, a pipette 36. The sperm traverse across a media 38 along the microfluidic chip 22, which may include the aforementioned glass 32, as well as a PMMA or other material layer 40, with a double-sided adhesive (DSA) layer 42 arranged there between to affix the glass 32 and PMMA layer 40 together. Ultimately, the sperm 34 traverse the microfluidic chip 22 to the outlet 16, where a mineral oil 44 may be found. Specifically, a thin layer of sterile, embryo-tested mineral oil may be placed on top of the media 38 in the inlet 14 and outlet 16 to avoid medium evaporation.

As illustrated, different channel lengths may be used or selected for effective sperm sorting. Furthermore, referring to FIG. 2C, a multichannel design may be utilized where the inlet 14 and collection chamber 16 are connected by multiple channels 46. As illustrated, a PBS collection buffer 48 may also be included, for example, to use in washings. Furthermore, the chip substrate housing the channels may be disposable.

Referring to FIGS. 2A and 2B, if included, lensless imaging can be used to record the shadow image of each individual sperm 34 onto an optoelectronic sensor array plane 31. This system 10 targets detecting/counting cells or monitoring in real-time the dynamic location of hundreds of thousands of individual cells on-chip over an ultra-wide FOV, for example, an FOV that is a few centimeters by a few centimeters. This technology provides these features with reduced complexity and ease of miniaturization.

One particular example of the system 10 including the imaging capabilities is illustrated in FIG. 2D. A standard microscope cannot monitor a whole microfluidic sorting chip and analyze sperm in real time. This challenge can be addressed by integrating lensless imaging with microchannels providing parallel on-chip monitoring and counting of sperm. The design permits miniaturization of this technology to make it suitable for an embryology/clinical lab and point-of-care settings.

The system 10, in the example in FIG. 2D, includes the light source 30 that is directed through an aperture 50 in the housing 12, such as a 50 μm aperture, to focus monochromatic light 52 toward a the microfluidic chip 22, across which the sperm 34 traverse, as described above. The system 10 may be coupled with a computer system 54 connected through a data connection 56, which may be wired or wireless, and a rechargeable battery or other power source 58 coupled through a power connection 60 to provide operational power for the imaging capabilities.

In one configuration, a combination of polymethyl-methacrylate (PMMA) of 1.5 mm thickness and double-sided adhesive (DSA) film of 50 μm thickness could be used to create microchannels. The DSA film can be cut to create microchannels of different lengths ranging from 5 mm to 40 mm using a laser cutter. Inlet and outlet ports extend through the PMMA with a diameter of 0.65 mm and 2 mm, respectively. The DSA film is then placed directly onto the PMMA in effect joining the two. A glass slide is placed onto the other side of the DSA film, such that the height of the channel is determined by the adhesive layer thickness. The larger outlet size is particularly designed to extract sorted sperm out of the channel easily accessible by a pipette. The distance between inlet and outlet determined the channel length. The length of the channel is defined as the distance between inlet and outlet.

To increase percentage of motile cells at the outlet and for high volume processing, a polycarbonate filter can be integrated into these microchips. This filter-based device can be designed using 3 mm thick PMMA cut to an area of 50 mm by 30 mm and another cut to an area of 30 mm by 30 mm. Cylinders of 20 mm diameter can be cut into both PMMA components and align vertically onto one another using 150 μm DSA. A 0.6 mm semen injection inlet is also cut into the larger device component at a 10 mm distance. The system can be assembled using a whatman nucleopore filter located between the two PMMA components.

Referring to FIGS. 1A through 2D, the system 10 can be used in large-scale semen processing. To do so, the sperm 34 is introduced through the inlet 14 to be place in the microfluidic chip 22. During this movement, the sperm 34 can be imaged using the light 30 and imaging sensor 31. The sperm 34 move toward the outlet 16. This outlet/collection chamber presents two chambers 24, 26. The first chamber 24 includes a filter presenting micropores and the second chamber 26 includes another filter including micropores. In this regard, the system 10 presents macro reservoirs 14, 16 connected by micropores to approximate the female genital track. Therein, the sperm 34 move collectively, influenced by each other, such as would naturally occur, along the medium 38 toward the outlet 16. The most motile, morphologically normal, mature, and functional sperm pass selectively through the micropores against gravity leaving behind dead or less functional sperm in the first chamber 24. That is, the sperm head is of spherical shape and has size of about 3 μm×4.5 μm. Sperm tails are about 45-50 μm long. If a filter having micropores of diameter larger than sperm head is placed in the first and second chambers 24, 26, only sperm that are motile can make their way through the micropores, whereas dead, dying, or damaged sperm cannot pass through the micropores because of their long tails. Instead, these dead, dying, and/or damaged sperm succumb to gravity and remain in the first chamber 24.

Thus, a microchip-based system is provided that is designed such that it does not require any centrifugation steps to retrieve healthy, motile, and morphologically normal sperm with minimal ROS generation. The device design makes sperm sorting procedure less labor intensive and inexpensive. The system incorporates utilizes exhaustion in space-constrained channels as a mechanism for sperm sorting. The system can isolate motile and morphologically normal sperm without any centrifugation step. Thus, a current coarse-grained model of sperm motility is used to model filter-based microfluidic devices in three dimensions, incorporating effects of cooperatively rising from hydrodynamic interactions between sperm, with channel walls, and with the filter surfaces and holes. This model allows the design of device parameters such as micropore size and incubation times.

The design and operation of the above-described system can be further appreciated from the following discussion of one example of a system, configuration for such system, and testing results of such system. This is but one example and is non-limiting in nature to the variety of configurations, designs, and operations that may be employed and fall within the scope of the present invention.

Example

Assembly of MMSS Chip

Figure 3:
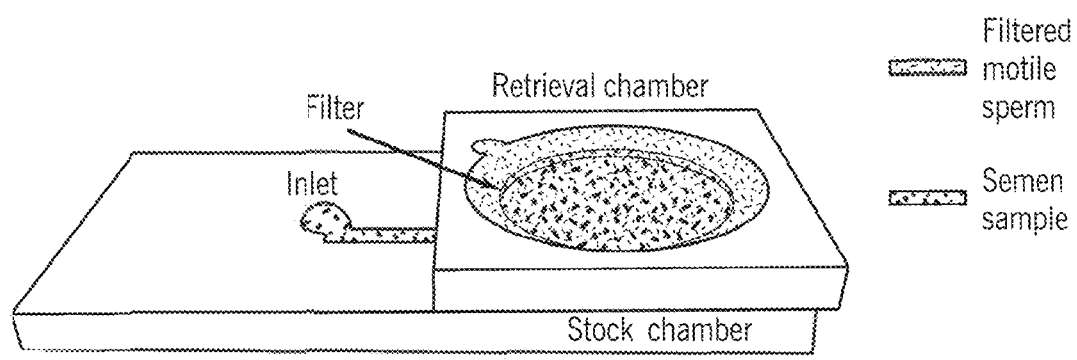
FIG. 3 is a perspective view of a prototype system for sorting sperm in accordance with the present invention.

The poly (methyl methacrylate) (PMMA, 3 mm thick; McMaster Carr, Atlanta, Ga.) and double side adhesive (DSA, 120 µm thick, St. Paul, Minn.) were cut using a laser cutter (Versa Laser™, Scottsdale, Ariz.). The design for the chip was generated on Coral Draw4 and implemented onto USLE Engrave software for cutting. Primary components of the MMSS chip included one 3 mm PMMA cut to an area of 50 mm×30 mm (bottom chamber) and another cut to an area of 30 mm×30 mm (top chamber). A 0.6 mm injection point was also cut into the bottom PMMA sheet at a 5 mm distance from the chambers. Cylinders of 20 mm diameter were cut into both PMMA components. The bottom PMMA chamber was first attached to glass slide using DSA. Top PMMA chamber was aligned and attached with bottom chamber using DSA. The Nuclepore™ track-etched polycarbonate membrane filters (Whatman Ltd, 25 mm diameter, 3 µm, 5 µm, 8 µm) were sandwiched between two PMMA chambers during chip assembly. Thus, it was considered that at least 1 µm and less than 10 µm may be a range of advantageous pore sizes. A perspective view of the assembled chip is shown in FIG. 3.

Sperm Sorting Using MMSS Chip

Thawed, unprocessed semen sample (stock sperm) was injected into the inlet of MMSS chip until it filled the first/bottom chamber. The first/bottom chamber was designed to hold up to 560 µl of the semen sample. In another set of experiments, the stock semen sample was diluted 4 times with 1 percent bovine serum albumin (BSA) in human tubal fluid (HTF) before injection into MMSS chip. Following injection, the first/upper chamber was topped off with 560 µl of 1 percent BSA in HTF. Chips were then stored at 37 degrees C. in incubator for 15, 30, 45, and 60 min intervals before fluid from top chamber was collected into eppendorph tubes for analysis.

Concentration and Motility Analysis

A standard Makler Haemocytometer was used to analyze the sperm samples for concentration and motility using optical microscope. Briefly, 1 µl of sperm sample was pipetted onto Makler Haemocytometer and covered with cover-lid provided with Haemocytometer. Sperm were counted by personnel familiar with method using a click-counter for at least three times. The sperm that were moving forward were considered motile.

Viability Analysis

The sperm samples were analyzed for viability using LIVE/DEAD® Sperm Viability Kit (L-7011, Molecular Probes®). SYBR 14 dye was used to stain live whereas Propidium Iodide (PI) was used to stain dead sperm. Samples were stained according to manufacturer's protocol. Briefly, first SYBR 14 dye was added into sperm sample to the final concentration of 100 nM. The sample was incubated for 5 min at 37° C. To stain the dead sperm, PI dye was added to the sample to the final concentration of 10 µM and allowed to incubate for 5 additional min. The sperm samples were smeared on a glass cover slip and imaged using fluorescent microscope Zeiss Axio Observer.Z1. Green and red emission filters were used for SYBR 14 and PI, respectively.

Velocity Measurement

Sperm samples were analyzed using the method described by WHO laboratory manual for sperm analysis. Briefly, sperm was retrieved from the MMSS chips (3 µm, 5 µm, 8 µm) after 30 min. Slides were prepared by putting 6 µl of sperm sample onto a glass slide and covered by using a 18×18 mm cover slip to give the sample a depth of 20.7 µm. To avoid drying up of samples, slides were made periodically, not simultaneously. Each slide was analyzed under 20× (Carl Zeiss) using light microscopy with live images of the sample being projected onto a computer monitor. Using a video capturing software (Snagit, TechSmith), movement of sperm samples were captured at random locations for 5 secs. Videos were converted to image sequences using VideotoJpeg software at 100 fps. The image sequence was input into ImageJ (National Institute of Health, http://rsbweb.nih.gov/ij/) for analysis using the CASA plugin to monitor sperm velocity parameters, i.e. straight line velocity (VSL), curvilinear velocity (VCL), and average path velocity (VAP).

Sperm Morphology Assessment

Recovered sperm suspension from 5 µm, and 8 µm MMSS chips were collected after 30 mins. Sperm retrieved from 3 µm MMSS chip were not analyzed for sperm morphology, as sperm concentration is too low for morphology analysis. A 10 µL sperm suspension was then taken and placed on a clean and sterile microscope slide and feathered smears were prepared. Smears were air dried and prepared for fixation. A Spermac staining protocol similar to the one provided by FertiPro was followed to stain sperm for morphology assessments. Briefly, dried smears were submerged into Spermac fixative solution for at least 5 min and then rinsed with DI water. Stain A was pipetted at one edge of the slides and allowed to flow over the smear. Slides were then placed on a flat surface and allowed to soak with stain for 1 min. The slides were then rinsed with DI water twice. Next, stain B was applied similarly to Stain A and allowed to penetrate sperm for 1 min. This was followed by a single rinse with DI water. Finally, stain C was pipetted over the smear and allowed to sit for 1 min before rinsing with DI water. At this point, at least 100 sperm were imaged using oil immersion and 100× objective (N (no. of repeats)=3). The sperm was considered morphologically normal if it falls within WHO morphology criteria (Head: spherical head; acrosome covering 40-70% of head area; head length 3.7-4.7 µm; head width 2.5-3.2 µm; length-to-width ratio 1.3-1.8; no more than 2 small vacuoles; post-acrosome region should not contain any vacuole. Midpiece: no residual cytoplasm in midpiece; length of midpiece should be approximately same as head length; no broken neck. Principal piece: no sharp angles or bends indicative of tail break; thinner than midpiece, length of principal piece should be approximately 10 times the head length).

Sperm Maturity Assessment

Recovered sperm suspension from 5, and 8 µm MMSS chips were collected after 30 mins. Sperm retrieved from 3 µm MMSS chip were not analyzed for nuclear maturity, as sperm concentration is too low for this analysis. Dried smears were fixed with the Spermac fixative solution for 5 min and subsequently rinsed with DI water. A 5% aniline blue in 4% acetic acid solution was prepared and was poured over smears. Smears were soaked for 5 min in staining solution and then rinsed with DI water. At least 100 sperm were assessed using oil immersion 100× objective (N (no. of repeats)=3). Sperm heads that stained dark blue were declared immature, while those that remained unstained were considered mature.

ROS Detection

Sperm Washing: 1 ml of semen was removed from a cryopreservation tank and thawed for 15 min in a 37° C. warm bath. Washed semen sample was prepared by adding 9 ml of HTF+1% ABSA media to 1 ml of semen, centrifuging for 500×g for 5 min and removing supernatant while leaving sperm pellet at the bottom of tube. This procedure was repeated three times. HTF media was added to sperm pellet and samples were stained with ROS studies.

Swim-up Method: 1 ml of semen was removed from a cryopreservation tank and thawed for 15 mins in a 37 desires C warm bath. The semen was diluted with 9 mL of HTF+1% BSA. The diluted sperm suspension was then centrifuged at 500×g for 5 mins. Following, the supernatant was removed and disposed. The remaining pellet was washed again by centrifuging sample at 500×g for 5 min. The supernatant was removed and disposed again. Finally, 500 µL of medium was added along the side wall of centrifuge tube while avoiding the disruption of the pellet. The sample was then placed in the incubator and motile sperm were allowed to swim up out of pellet for 30 min. The motile sperm were collected by leaving pellet behind. MMSS chips were incubated for a 30 mins period and sperm suspension was recovered for ROS studies.

Staining for ROS detection: ROS generation was examined by using flow cytometry in conjunction with two fluorescent dyes, dyhydroethidium (DHE) and SYTOX green. DHE reacts with the superoxide anion which produces two fluorochromes which bind to sperm DNA and produces a red fluorescence. While SYTOX green is indicative of cell viability, it produces a green fluorescence when the cell is dead. For this experiment, four control samples were prepared in which all consisted of 200 µL of recovered sperm suspension mixed with 20 µL of hydrogen peroxide. This was followed by an incubation at 37 degrees C. for 30 mins. The dyes were added to the samples; no dye for negative control, DHE at 5 µM was added to the second sample, SYTOX green at 50 nM was added to the third sample, and the fourth sample contained both DHE and SYTOX at 5 µM and 50 nM respectively. Dyes were incubated for 15 mins and then transferred to the flow cytometer for measurement 15 min prior to test samples. FACSCalibur flow cytometer (Becton Becton Dickinson, San Jose, Calif.) was used during experiments. Argon laser excitation at 488 nm was coupled with emission measurements using 530/30 band pass (green) and 585/42 band pass (red) filters for FL1 and FL2, respectively. Non-sperm events were gated out, and at least 10,000 cells were examined. For test samples, 500 µL sample from thawed semen, the swim up suspension, 3, 5, and 8 µm filter pore size microchips were collected. DHE and SYTOX at 5 µM and 50 nM respectively were added to each sample and allowed to incubate for 15 min. Samples were taken to the flow cytometer for measurement.

DNA Fragmentation

TUNEL assay kit (In Situ Cell Death Detection Kit, Fluorescein by Roche Applied Science) was used to quantify DNA fragmentation for raw semen, swim-up, and retrieved sperm population from microchip devices with filters of 3, 5 and 8 µm pore size. All these samples were attained as previously mentioned in ROS Detection section. Initially, all the sperm suspensions were washed twice by centrifuging at 500×g for 5 min with PBS and 1% BSA. Once washed, the concentrations of sperm cells were adjusted to $2\times10^6$ cells/ml. Sperm suspensions were then fixed with 4% paraformaldehyde in PBS (200 µL for every 100 µL of cell suspension) for 30 min at room temperature. Sperm cells were washed twice at 500×g for 6 min with PBS and 1% BSA and permeabilized with 0.1% TritonX in 0.1% sodium citrate for 2 min in/on ice. Sperm were washed twice followed by 1 hour incubation at 37° C. with 5 µL of enzyme (TdT) solution and 45 µL of label (dUTP-Flourescein) solution. Similarly, a negative and positive control sample was prepared. However, prior to staining, the positive control was incubated with DNase for 40 min at 37° C. During staining, the negative control was only incubated with label solution (without enzyme solution). After staining, samples were washed twice with PBS and 1% BSA and resuspended in PBS (Muratori et al, 2000). Fluorescence emission of DNA fragmented cells were assessed with flow cytometer and detected by the FL-1 detector (521 nm). A total of 5000 events were acquired. Sperm population was gated out from data to eliminate any signal from debris. Experiments are repeated 6 times (N=6).

Results and Discussion

Figure 4:
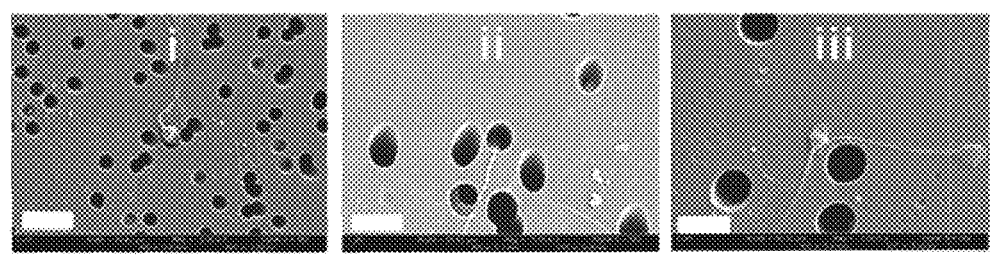
FIG. 4 is a series of images of sperm acquired using the present invention.

To develop a chemical-free and centrifugation-free, high-throughput, vertical sperm sorting device, the MMSS chips were fabricated and assembled as described above. Briefly, it is a two-chamber chip separated by polycarbonate filters of various diameters, such as, for example, 3, 5, 8 µm. The sperm sample was injected into the bottom chamber and sorted motile/healthy sperm were collected from the top retrieval chamber. The presence of the filters with, for example, uniform sized pores between two chambers was designed such that the most motile and healthy sperm could translocate through the filter pores. Scanning electron microscope (SEM) images of polycarbonate filters used for sperm sorting showed uniform pore diameters as shown in FIG. 4. SEM images of polycarbonate nuclepore track-etched membrane filters of different micropore diameters, i) 3 µm ii) 5 µm and iii) 8 µm. The scale bar is 10 µm. These images shows the comparative size of various filter pores and sperm.

The sperm head is of spherical shape and has size of about 3 µm×4.5 µm. Sperm tail is about 45-50 µm long. If a filter of diameter larger than sperm head is placed between this two-chamber chip, only sperm which are motile can make their way through the micropores whereas dead/dying sperm cannot pass through the micropores because of their long tails.

Sperm Motility and Retrieval Rate

To investigate the motility of the sorted sperm, we analyzed the sperm collected from the top retrieval chamber of all three MMSS chips (3, 5, and 8 µm diameter filter chips).

Results showed that the sperm sorted with MMSS chips showed significantly higher motility as compared to stock sperm sample, such as illustrated in FIG. 5A. Specifically, the 3, 5, and 8 µm filter chips showed sperm motility of greater-than-or-equal-to 95 percent±10, greater-than-or-equal-to 90.4 percent±1.8, greater-than-or-equal-to 85.9 percent±1.5, respectively, which was significantly higher than the stock sperm motility (39.8 percent±1.9). We further investigated the effect of incubation time on sperm motility. Sperm were collected after 15, 30, 45 and 60 mins. We found that the motility of the retrieved sperm increased when sperm sample was collected after a longer period of time; motility in the case of 60 mins time point was highest whereas it was lowest for 15 minutes time points, such as illustrated in FIG. 5A. This increased motility is noticed in all three chips. When HTF+1 percent BSA was pipetted to the top chamber of the MMSS chip at the start of each experiment, slight turbulence would produce in the sperm sample due to mixing of the two liquids; stock sperm sample and HTF+1 percent BSA media. This turbulence in sperm sample is the possible reason for the lesser sperm motility at the start of the experiment (after 15 mins) as compared to latter time points (after 30, 45, and 60 mins). In addition, we calculated the sperm retrieval rate at various time points, that is, percentage (%) of healthy sperm retrieved out of stock sample. Retrieval rate is an important parameter for any sperm sorting device especially for the situation where sperm samples have low sperm count (oligospermic and azoospermic specimens). In the MMSS chip, the sperm retrieval rate was analyzed over a period of time; 15, 30, 45, and 60 min time points is illustrated in FIG. 5B. Sperm retrieval rate was maximum for samples collected after 30 mins time points (3.08 percent±0.42, 23.75 percent±3.96, and 28.58 percent±2.81 for 3, 5, and 8 µm MMSS chips, respectively). We call this 30 minutes time point as a saturation time point as sperm retrieval rate was reduced if the sample was incubated for more than 30 minutes, such as illustrated in FIG. 5B. We believe that some of the sperm might be travelling back through the filter into bottom chamber after 30 minutes.

Sperm Viability

Motile sperm are considered viable. To substantiate our finding that the sorted sperm are viable, we performed the live/dead staining for sorted sperm for 30 min time point. The viability of sorted sperm was significantly higher than stock sperm sample; 41.0 percent±0.45 (stock sperm), 91.32 percent±3.43 (3 µm MMSS chip), 89.83 percent±5.82 (5 µm MMSS chip), 91.59 percent±4.44 (3 µm MMSS chip).

Effect of Sample Dilution on Sperm Motility and Retrieval

To investigate the effect of sperm sample dilution on motility and retrieval rate, we diluted the stock sperm sample with HTF+1 percent BSA at the ratio of 1:4 before processing using MMSS chips. The motility of the sorted sperm was significantly higher than stock sperm sample at all 4 time points (15, 30, 45, and 60 mins); 45.8 percent±1.5 (stock sperm), ≥95.0 percent±5.0 (3 µm MMSS chip), ≥93.7 percent±4.7 (5 µm MMSS chip), ≥90.7 percent±2.5 (8 µm MMSS chip), whereas it was not different than if undiluted sperm sample was used, as shown in FIG. 5A. However, the sperm retrieval rate increased if diluted sperm sample is used instead of undiluted stock sperm, as shown in FIG. 5B. Maximum retrieval rate was found to be 52.68 percent±4.97 for 8 µm chip after 30 minutes time point. In diluted sample, sperm has increased mean free path before hitting another sperm. This phenomena might has helped sperm in reaching and crossing the filter micropore faster. Secondly, the filter has fixed number of pores (<14 percent porosity). As lesser number of sperm were trying to cross the filter pores in diluted sample, it was more probable for each sperm to find an empty pore and translocate through it.

Sperm Velocity Analysis

Various sperm velocity parameters were analyzed, i.e. curvilinear velocity (VCL), straight line velocity (VSL), and average path velocity (VAP). A representative image of sperm track showing these velocity definitions is shown in Supplementary FIG. 3. The original sperm video from which FIG. 3 track is generated is given as Supplementary Movie 1. The sorted sperm using MMSS chips showed significantly higher sperm velocities than stock sperm sample, as illustrated in FIG. 6. Specifically, average sperm VCL was increased from 52.7±6.0 µm/sec (stock sperm) to 59.9±3.5 µm/sec, 75.3±3.1 µm/sec, and 75.6±4.5 µm/sec for 3, 5, and 8 µm MMSS chips, respectively, as illustrated in FIG. 6A. Average sperm VSL increased from 44.4±5.6 µm/sec (stock sperm) to 52.1±3.5 µm/sec, 63.4±3.5 µm/sec, and 64.1±3.9 µm/sec for 3, 5 and 8 µm chips, respectively, as illustrated in FIG. 6B. Average sperm VAP increased from 48.4±5.8 µm/sec (stock sperm) to 54.1±3.4 µm/sec, 68.0±2.9 µm/sec, and 67.5±4.1 µm/sec for 3, 5, and 8 µm chips, respectively, as illustrated in FIG. 6C. Higher sperm velocities indicate that the sorted sperm are healthier than stock sample. When we compared velocities among the sperm sorted using three different MMSS chips, it was noticed that sperm sorted using 5 and 8 µm MMSS chips gave higher VCL, VSL, and VAP velocities than 3 µm filter chip. This is probably due the fact that mostly immature motile sperm having head sizes smaller than 3 µm could pass through the 3 µm micropores. Only exception to this was the filter areas where two or more 3 µm pores were joined together to make up a larger pore.

Sperm Morphological Analysis

For morphological analysis, sperm were stained with Spermac Stain. Sperm were considered morphologically normal based on the strict criteria defined by WHO. Any sperm sample having >4 percent morphologically normal sperm is considered normal. We found that sperm sorted using 5 µm MMSS chips did not improve the sperm quality in term of overall morphology, though the sorted sperm were motile. Sperm sorted using 8 µm MMSS chips showed significantly improved morphology over stock and sperm sorted using 5 µm MMSS chip; 30.0 percent±7.6 (8 µm MMSS chip), 17.0 percent±3.2 (5 µm MMSS chip), and 17.6 percent±0.5 (stock sperm).

Sperm Nuclear Maturity Analysis

Figure 7:
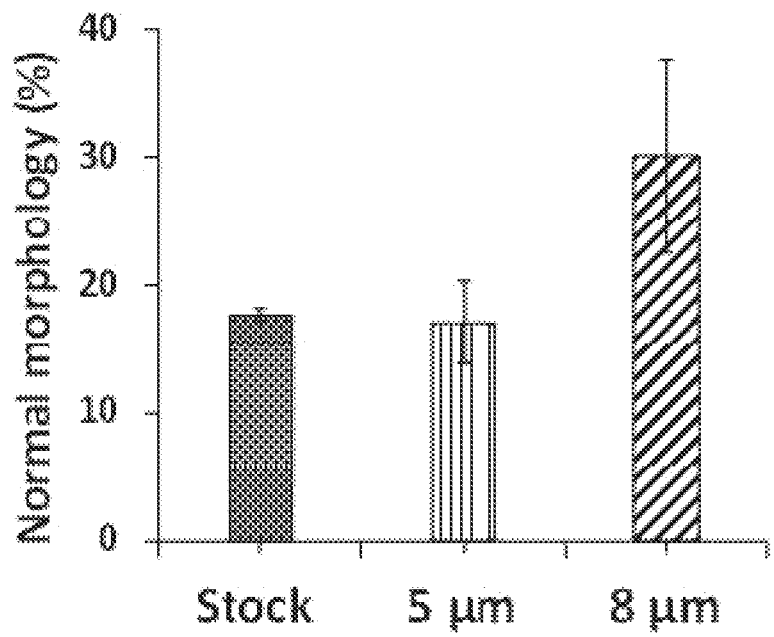
FIG. 7 is a graph showing normal morphology (%) for stock and sorted sperm.
Figure 8:
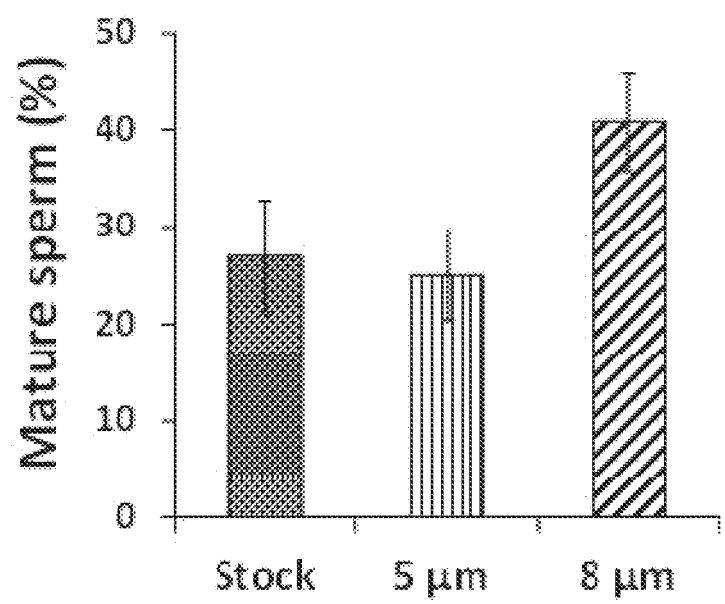
FIG. 8 is a graph showing mature sperm percentage calculated for stock and sorted sperm.

Sperm were stained with aniline blue and analyzed for nuclear maturity. Aniline blue staining can discriminate the lysine-rich nuclei of immature sperm and arginine/cysteine-rich nuclei of mature sperm. The nuclei of immature sperm were stained with aniline blue and showed a color contrast between nuclei and acrosome. Representative images of sperm stained with aniline blue and their assessment criteria is shown in FIG. 7. Sperm sorted using 5 µm filter chip did not show any improvement over stock sperm in terms of nuclei maturity. Whereas, sperm sorted using 8 µm filter chip showed higher nuclear maturity than stock sperm sample, as shown in FIG. 8; 40.8 percent±5.1 (8 µm MMSS chip), 25 percent±4.6 (5 µm MMSS chip), and 26.9 percent±5.8 (stock sperm).

ROS Generation Analysis

Sorted sperm was analyzed for ROS generation. We have compared the ROS generation in the sperm after washing method, conventional swim-up method and MMSS chips. We found that sperm sorted by MMSS chips produced significantly lesser ROS than swim-up and washing method (FIG. 9). Sperm washing and swim-up method produced ROS in 10.1%±0.3% and 10.6%±1.1% of the sperm respectively, whereas sperm sorted using MMSS chips showed ROS production in only 0.8%±0.4% (3 µm MMSS chip), 0.7%±0.1% (5 µm MMSS chip) and 1.0%±0.1% (8 µm MMSS chip) of the sperm. Unsorted semen sample showed ROS generation in 1.8%±0.6% of the sperm, which clearly indicated that the increased generation of ROS in swim-up and washing methods came from centrifugation steps.

DNA Fragmentation Analysis

The analysis of sperm DNA fragmentation can differentiate fertile and infertile men, and sperm samples showing higher level of DNA fragmentation results lower fertilization rates in IVF/ICSI, impaired embryo progression and lower pregnancy rates. Sperm sorted using MMSS chips were analyzed for DNA fragmentation. DNA fragmentation (%) was 1.1%±0.3% (8 µm MMSS), 2.1%±0.7% (5 µm MMSS chip), 3.4%±0.8% (3 µm MMSS chip), 3.7%±1.2% (swim-up method), and 31.2%±1.2% (unsorted semen). The sorted sperm using 5 µm and 8 µm chips showed significantly lower DNA fragmentation (%) than unsorted semen sample and sperm sorted using swim-up method (FIG. 10).

DISCUSSION

The ideal sperm sorting technique should (i) be rapid and cost-effective, (ii) be less labor intensive, (iii) process larger sperm volumes, (iv) have higher retrieval efficiency to isolate motile sperm from dead/non-motile sperm, (v) isolate sperm with higher velocity, (vi) isolate morphologically normal and mature sperm, (vii) reduce ROS generation and morphological damage by eliminating centrifugation steps, (viii) reduce the percentage of sperm DNA fragmentation. These parameters are generally desirable features for any sperm-sorting device and the system of the present invention offers a platform providing these features.

In the particular example provided herein, the total material cost to fabricate one chip is less than a dollar (50 cents for filter, <50 cents for PMMA and DSA). The MMSS chip rapidly (approximately 30 minutes) isolated motile sperm from non-motile ones with the higher retrieval rate (28.58 percent±2.81 percent retrieval from stock sperm) than swim-up technique (<20 percent). The retrieval was further increased to 52.68 percent±4.97 (8 µm filter) by using diluted sample. Although sperm dilution gave higher retrieval of healthy sperm, it reduced the actual stock sperm volume that could be processed at a time. The stock sperm may be desirably diluted before processing for (i) low volume ejaculates, and (ii) ejaculated with very low sperm count. MMSS chip design is highly scalable and can process large semen volumes by using larger filters (for example, 1.5 ml). Processing a large semen sample is needed to retrieve enough sperm for IVF procedures. Furthermore, high volume processing is very important for the samples having low sperm count or low sperm motility.

Sperm having higher velocity parameters can increase the ICSI fertilization rates. Sperm sorted by MMSS chip showed significantly enhanced velocity parameters (VCL, VSL and VAP) compared to stock sperm that clearly demonstrated that sorted sperm were of higher quality. Sperm morphology is another important indicator for a successful fertilization. Morphologically normal sperm increase the fertilization rate during IVF procedures. Sorting sperm using 8 µm MMSS chip improved sperm morphology by 1.7 folds, which is a significant improvement, as illustrated in FIG. 7. It is also interesting to note down the association of sperm motility and morphology. We found that morphologically normal sperm also showed better velocities, which demonstrated that these two functional parameters (sperm velocity and morphology) are associated.

Sperm nuclear maturity has shown an association with male infertility. Chromatin condensation as described by nuclear maturity is another predictor for IVF outcome. Sperm sorted using 8 µm MMSS chips showed significantly improved sperm maturity compared to stock sample, as illustrated in FIG. 8. We also looked into the ROS generation by human sperm. ROS generation is an important investigative tool to assess the sperm quality and its apoptosis status. There are many pathways and reasons leading to sperm ROS generation such as poor differentiation during spermiogenesis, poor chromatin compactness, exposure to heavy metals, heat or electromagnetic radiations, prolonged in vitro culture, and presence of sperm in the vicinity ROS generating cells. Conventional techniques utilizing centrifugation steps to sort healthy sperm is another reason for ROS generation as these techniques centrifuge sperm with ROS generating cells such as leukocytes. We found that sperm sorted using all three MMSS chips showed significantly low ROS generation compared to stock sperm.

DNA fragmentation is another very important indicator for male infertility. According to some reports, sperm DNA integrity can be considered as an independent marker for fertilization. Sperm sorted using MMSS chips showed a significant improvement in DNA fragmentation compared to unsorted semen sample, as shown in FIG. 10. Currently, sperm swim-up method is considered standard to sort sperm with lower DNA fragmentation. It is interesting to note here that the sperm sorted with 5 and 8 µm MMSS chips showed ever lower DNA fragmentation than swim-up method. We believe based on these functional assays that the sperm sorted using 8 µm MMSS chip are of better quality compared to conventional methods. The sorting of morphologically normal, mature, motile and functional sperm would potentially improve IVF/ICSI outcomes.

Figure 11:
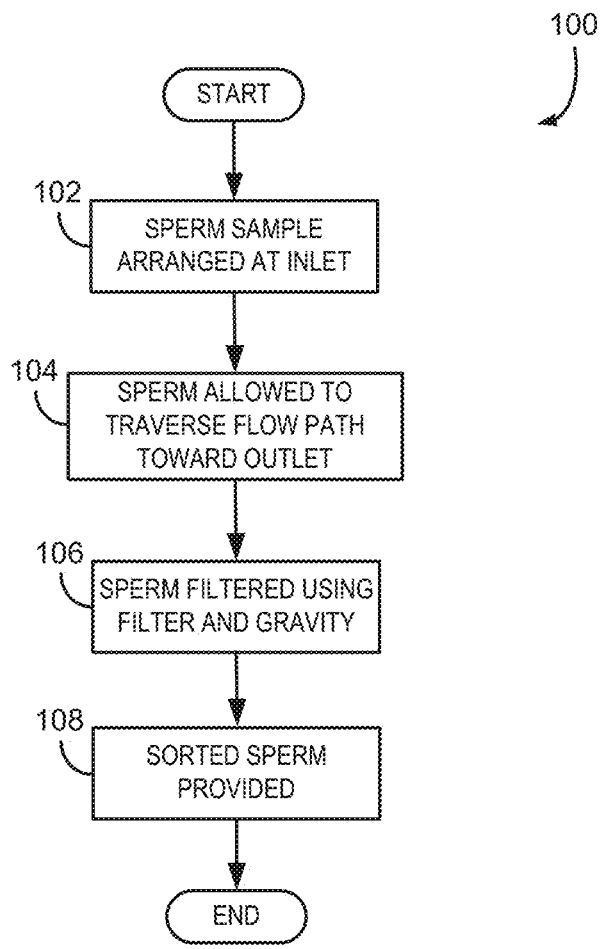
FIG. 11 is a flow chart setting forth an example of some steps in accordance with the present disclosure.

Referring now to FIG. 11, some example steps 100 in a process for sorting sperm are provided. The steps 100, beginning at process block 102, include receiving a sample of sperm to an inlet of a microfluidic system, such as described above. Thereafter, at process block 104 the sperm of the sample are allowed to traverse a flow path through the microfluidic system toward an outlet providing access to the microfluidic system for harvesting of sorted sperm from the microfluidic system. At process block 106, the sperm are subjected to a filter prior to reaching the outlet. As described, the filter has a plurality of micropores and is oriented restrict movement of the sperm through the filter using gravity. Thus, at process block 108, sorted sperm is provided at the outlet. The sorted sperm includes sperm passing to the outlet after passing through the filter and overcoming gravity.

Thus, the present disclosure provides system and methods for (i) development of a chemical free and flow free system to sort healthy sperm, analyze motility, speed and morphology, (ii) isolation of the sorted healthy sperm, and (iii) developing a better understanding of exhaustion and collective motion of sperm. This platform is an innovation beyond the existing clinical procedures such as the swim-up and microdrop techniques. It is also novel beyond the reported microfluidic based sperm sorting devices, as it uses a new ground-breaking knowledge of exhaustion in space-constrained channels for sorting and analyzing sperm. Given that clinical reproductive medicine has been a challenging field that is labor intensive, such an easy-to-use microchip can lead to improved selection of healthy sperm and decreased dependence on operator skills, facilitating repeatable, and reliable operational steps.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for sorting sperm, comprising:
a housing including a lower component and an upper component coupled together;
a fluidic system supported by the housing;
an inlet extending through the lower component and providing access to the fluidic system to deliver sperm to the fluidic system;
a collection chamber configured to pass motile sperm for harvesting and restrict non-motile sperm, the collection chamber including a first chamber extending through the lower component and a second chamber extending through the upper component and positioned above the first chamber;
at least one channel extending from the inlet to the collection chamber to allow sperm delivered to the fluidic system through the inlet to progress along a flow path toward the collection chamber;
a filter including a plurality of micropores and arranged in the collection chamber to cause sperm traveling along the flow path to move through the filter and against gravity to reach the second chamber, wherein the filter is located between the upper component and the lower component; and
an additional collection chamber extending into the upper component and connected to the second chamber, the additional collection chamber sized and configured to facilitate harvesting functional sperm out of the additional collection chamber, wherein the functional sperm are suitable for fertilization and are at least some of the motile sperm.

2. The system of claim 1, wherein the plurality of micropores are sized to permit a head of the sperm to pass therethrough.

3. The system of claim 1, wherein the plurality of micropores are at least 1 um and less than 10 um in diameter.

4. The system of claim 1, wherein the fluidic system is configured such that some of the motile sperm pass through the filter into the second chamber and traverse a path from the second chamber into the additional collection chamber in a flow-free manner, and wherein the second chamber is connected to the additional collection chamber by a fluid connection channel and no other channels extend from the second chamber.

5. The system of claim 4, wherein the additional collection chamber does not comprise a filter.

6. The system of claim 1, wherein a top portion of the second chamber of the collection chamber is an open outlet that provides access to the fluidic system.

7. The system of claim 6, further comprising sperm arranged at the inlet.

8. The system of claim 6, further comprising sperm within the at least one channel but not above the filter.

9. The system of claim 1, wherein the additional collection chamber does not comprise a filter.

10. The system of claim 1, further comprising a slide supporting the housing, wherein the slide is located under the lower component and forms a lower surface of the at least one channel.

11. The system of claim 1, wherein the filter is a polycarbonate filter.

12. The system of claim 1, wherein the second chamber is connected to the additional collection chamber by a fluid connection channel and no other channels extend from the second chamber.

13. A method for sorting sperm, comprising:
delivering a sample of sperm into an inlet connected to a fluidic system comprising a housing including a lower component and an upper component coupled together, wherein the inlet extends through the lower component and provides access to the fluidic system to deliver sperm to the fluidic system;
allowing sperm in the sample of sperm to traverse a flow path through the fluidic system from the inlet to a collection chamber, wherein the collection chamber includes a first chamber formed by the lower component, and a second chamber positioned above the first chamber and formed by the upper component, wherein the first chamber and the second chamber are separated by a filter positioned in the collection chamber, wherein the filter has a plurality of micropores sized to permit a head of the sperm to pass therethrough, and wherein the second chamber is connected to an additional collection chamber by a fluid connection channel and no other channels extend from the second chamber;
allowing at least some motile sperm from the sample of sperm that have entered the collection chamber to selectively pass through the filter against gravity to traverse a path into the second chamber and then to traverse a path into an additional collection chamber; and
harvesting functional sperm from the additional collection chamber, wherein the functional sperm are suitable for fertilization and are at least some of the motile sperm that have passed through the filter and into the additional collection chamber, wherein the fluidic system is configured such that some of the motile sperm pass through the filter into the second chamber and move from the second chamber into the additional collection chamber in a flow-free manner.

14. The method of claim 13, wherein the first chamber extends through the lower component and the second chamber extends through the upper component.

15. The method of claim 14, wherein the filter is located between the upper component and the lower component.

16. The method of claim 15, wherein a top of the second chamber is an open outlet that provides access to the fluidic system as the motile sperm traverse the flow path through the fluidic system from the inlet to the collection chamber.

17. The method of claim 15, wherein the collection chamber is connected to the additional collection chamber by a fluid connection channel, and no other channels extend from the additional collection chamber.

18. The method of claim 15, wherein the additional collection chamber does not comprise a filter when the at least some of the motile sperm are harvested.

19. The method of claim 13, wherein a top of the second chamber is an open outlet that provides access to the fluidic system as the motile sperm traverse the flow path through the fluidic system from the inlet to the collection chamber.

20. The method of claim 13, wherein a higher percentage of motile sperm are present at the additional collection chamber than in the sample when the at least some of the motile sperm are harvested.

21. The method of claim 13, wherein the additional collection chamber does not comprise a filter when the at least some of the motile sperm are harvested.

22. The method of claim 13, wherein the plurality of micropores are at least 1 um and less than 10 um in diameter.

23. The method of claim 22, wherein the filter is located between the upper component and the lower component.

* * * * *